(12) United States Patent
Pagenkopf et al.

(10) Patent No.: US 7,034,163 B2
(45) Date of Patent: Apr. 25, 2006

(54) SYNTHESIS OF PYRROLES

(75) Inventors: Brian L. Pagenkopf, Austin, TX (US); Ming Yu, Austin, TX (US)

(73) Assignee: Board of Regents The University of Texas System, Austin, TX (US)

( * ) Notice: Subject to any disclaimer, the term of this patent is extended or adjusted under 35 U.S.C. 154(b) by 0 days.

(21) Appl. No.: 10/656,867

(22) Filed: Sep. 5, 2003

(65) Prior Publication Data

US 2005/0054857 A1    Mar. 10, 2005

(51) Int. Cl.
*C07D 207/06*    (2006.01)

(52) U.S. Cl. ...................................... 548/531

(58) Field of Classification Search ................ 548/453, 548/492, 531
See application file for complete search history.

(56) References Cited

OTHER PUBLICATIONS

Ming Yu et al., A Powerful New Strategy for Diversity-Oriented Synthesis of Pyrroles from Donor-Acceptor Cyclopropanes and Nitriles, "Organic Letters", vol. 5, No. 26, PP 5099-5101 (2003).*
Christiane Bruckner et al., A novel Synthesis of Pyrrole derivatives, "Liebigs Annalen der Chemie" vol. 5, pp. 471-473, (1988).*
Ming Yu et al., Synthesis of 2,2'-Bipyrroles and 2,2'-Thienylpyrroles form Donor-Acceptor Cyclopropanes and 2-Cyanoheteroles, "Organic Letters", vol. 6, No. 6, pp. 1057-1059 (2004).*

* cited by examiner

*Primary Examiner*—Johann Richter
*Assistant Examiner*—Ebenezer Sackey
(74) *Attorney, Agent, or Firm*—Gardere Wynne Sewell LLP

(57) ABSTRACT

An improved and highly efficient method for the preparation of 2-R(R=alkyl, aryl, H) pyrroles from nitrites (RCN, R=alkyl, aryl) is described using Lewis acid activated donor-acceptor cyclopropanes to react with aliphatic, aromatic, branched, α,β-unsaturated, or otherwise functionalized nitrites in a cascade [3+2] dipolar cycloaddition, dehydration and tautomerization sequence.

9 Claims, No Drawings

SYNTHESIS OF PYRROLES

This application was funded, in part, by the Department of Defense Prostate Cancer Research Program, DAMD17-01-1-0109, which may have certain rights.

BACKGROUND OF THE INVENTION

The present invention is directed to the field of organic chemistry in general and specifically to the preparation of pyrroles.

Pyrroles are important heterocycles that occur in porphyrins, pigments and other natural products, have found applications in materials science, and are common components in molecular recognition and self-assembly ensembles. Pyrrole may be synthesized a number of ways, often using classic condensation reactions between activated methylenes and amino ketones. However, these reactions are limited by their inefficiency, functional group incompatibility or the limited variety of substituents that can be introduced around the pyrrole. For example, classic pyrrole syntheses suffer from cross coupling side reactions and work best only with symmetrical pyrroles.

More recent pyrrole syntheses reactions typically utilize specialized methodologies that, themselves, are also limiting. Alternatively, the reactions excel at accessing one substitution motif, but are cannot be used for other substitution motifs. As a result, there is no single strategy for efficiently preparing all combinations of substituted pyrroles from readily available materials. Thus, there is a need for improved synthetic techniques that may be used with materials that are known and easy to handle in order to allow the preparation a large variety of pyrroles. It is also desirable that the new methods be efficient and stereoselective. Importantly, there is a need for synthetic methods that are flexible and that offer access to pyrroles that are difficult to prepare by standard methods.

SUMMARY OF THE INVENTION

The present invention solves many problems associated with current synthesis methodologies for preparing pyrroles and overcomes problems associated with an inability to introduce new functional groups that are not always compatible with the reaction conditions used with current methodologies.

One form of the present invention is the preparation of one or more pyrroles from nitrites and cyclopropanes through a formal 3+2 cycloaddition as shown below:

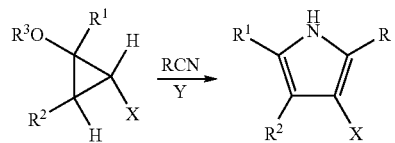

where R, $R^1$, $R^2$, and $R_3$ are each independently aryl or alkyl groups or H; the nitrile (RCN) is aliphatic, aromatic, branched, $\alpha,\beta$-unsaturated, or otherwise functionalized; X is an ester or ketone; and Y is a Lewis acid.

Another form of the present invention is an improved and efficient synthesis of di-, tri- and tetrasubstituted pyrroles as shown below:

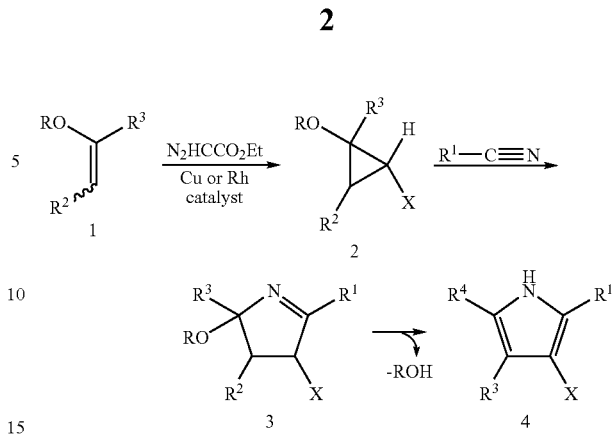

where RO is a carboxylate groups; $R^1$, $R^2$, $R^3$ and $R^4$ are each independently aryl or alkyl groups or H; the nitrile is aliphatic, aromatic, branched, $\alpha,\beta$-unsaturated, or otherwise functionalized; X is an ester or ketone; and Y is a Lewis acid.

With the present invention, there is absolute control over substituents at C(2), a feature of the invention that reflects the use of a nitrile precursor. This ability to control the substituent at C(2) in a way that provides unambiguous differentiation from C(5) is key in many of the applications of pyrrole. As used herein, both aliphatic and aromatic nitrites are effective.

An added feature of the present invention is that it simplifies the preparation of many classes of pyrroles and offers access to structures that are otherwise difficult or expensive to prepare; thus, facilitating the use of new pyrroles in more productive and cost-effective ways.

DETAILED DESCRIPTION OF THE INVENTION

Although making and using various embodiments of the present invention are discussed in detail below, it should be appreciated that the present invention provides many inventive concepts that may be embodied in a wide variety of contexts. The specific aspects and embodiments discussed herein are merely illustrative of ways to make and use the invention, and do not limit the scope of the invention.

The present uses a [3+2] cycloaddition strategy for the preparation of hetereocycles and, as such, is an improved and even more efficient method of synthesizing substituted pyrroles (Scheme 1).

Scheme 1

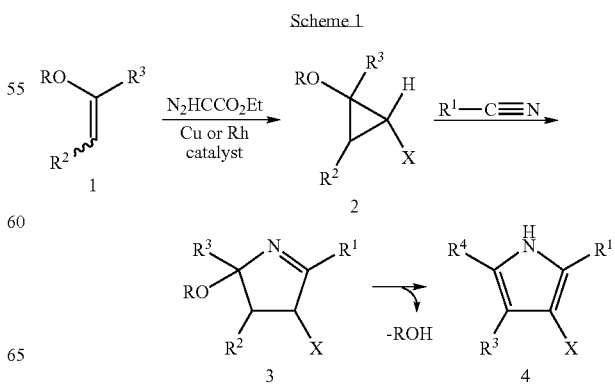

where RO is a carboxylate group; $R^1$, $R^2$, $R^3$ and $R^4$ are each independently aryl or alkyl groups or H; the nitrile is aliphatic, aromatic, branched, α,β-unsaturated, or otherwise functionalized; X is an ester or ketone; and Y is a Lewis acid.

In general, the present invention reacts cyclopropanes with nitriles. In preparing the pyrrole, the synthesis reaction places a carboxylate group at C(3) (and, if required, easily removed by standard pyrrole chemistry). The C(4) and C(5) groups can be hydrogen, or substituted independently of each other. By use of a nitrile precursor, there is also absolute control over substituents at C(2) that provides unambiguous differentiation from C(5). Importantly, a very large number of pyrroles can be easily prepared from a single cyclopropane precursor. In fact, the present invention is ideally suited for preparing chemical libraries due to such diversification at C(2). In this application the standard numbering convention for the positions in the pyrrole ring is used.

Additional features of the present invention include: (a) either the 2- or 5-C position are substituted (substitutions coming from nitrile); (b) electron neutral and electron rich nitriles participate in the reaction and nitriles can be aliphatic, branched, α,β-unsaturated, aryl, and functionalized; (c) cyclopropanes, compounds that are easy to make, are used for the reaction; (d) C(2) serves as an electron withdrawing group; (e) position 4, 5 or both can be H; (f) most groups (in addition to Me) are easily installed at the C(4) or C(5) positions; (g) functional groups elsewhere on the cyclopropane or the nitrile are well tolerated; and (h) di- and tri-pyrroles can be prepared in a single step from readily available materials.

EXAMPLES OF PYRROLE SYNTHESIS

Many model substrates are amenable for the present invention. One model substrate is the unsubstituted donor-acceptor cyclopropane 5 (see Table 1). The ability to use nitrites as a solvent is another feature of the present invention. As such, a variety of nitrites may be used in the present invention, such as aliphatic, aromatic and α,β-unsaturated nitrites.

A Lewis acid that is effective for catalyzing the desired cycloaddition reaction to produce a pyrrole facilitates activation of the reaction. One such Lewis acid found to promote high product yields is trimethylsilyl trifluoromethanesulfonate ($Me_3SiOTf$). For example, cyclopropane activation may occur with the addition of $Me_3SiOTf$ to a solution of 5 in acetonitrile to produce the pyrrole in 80% isolated yield (Table 1, entry 1; yields based on cyclopropane). As shown in Table 1, the inclusion of other solvents provide variable yields (e.g. 73% with nitromethane). Use of nitrile solvents depend primarily on more practical considerations such as the type of cyclopropane compound that is employed.

Examples of other reaction conditions using other nitrites include the following: adding 1 equivalent of $Me_3SiOTf$ to a solution of cyclopropane and 10 equivalents of nitrile in either dichloromethane, nitromethane or nitroethane solvent at or below ambient temperature. Butyronitrile, for example, provides a yield similar to that obtained with acetonitrile (Table 1, entry 2; yield 77%). In addition, both aromatic nitrites (Table 1, entries 3 and 4) and α,β-unsaturated nitrites (Table 1, entries 5–7) participate in the reaction. Products from reactions across the double bond of an unsaturated nitrile were not detected.

TABLE 1

Pyrroles from DA Cyclopropane Nitrile Cycloadditions.

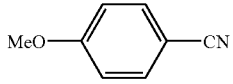

| Entry | Nitrile | Pyrrole | IsolatedYield |
|---|---|---|---|
| 1 | MeCN | R = Me | 80% |
| 2 | PrCN | R = Pr | 77% |
| 3 | PhCN | R = Ph | 35% |
| 4 | 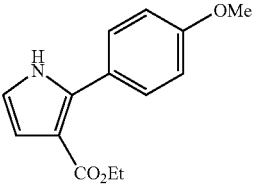 | 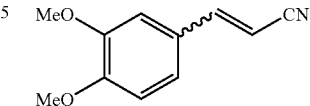 | 55% |
| 5 | 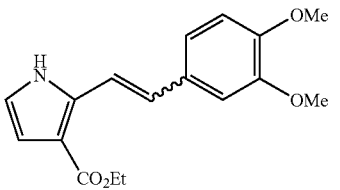 | | 85% |

TABLE 1-continued

Pyrroles from DA Cyclopropane Nitrile Cycloadditions.

nBuO—cyclopropane(H, CO₂Et, H) 5 →[TMSOTf, RCN]→ pyrrole(NH, R, CO₂Et) 6

| Entry | Nitrile | Pyrrole | Isolated Yield |
|---|---|---|---|
| 6 | Ph–CH=CH–CN | 2-styryl-3-(CO₂Et)pyrrole | 39% |
| 7 | MeO–CH=CH–CN | 2-(CH=CH–OMe)-3-(CO₂Et)pyrrole | 91% |

The examples in Table 2 illustrate the power of the present invention method to install groups (e.g., alkyl groups) selectively at either C(4), C(5) or both of these positions without formation of constitutional isomers. In Table 2, entries 1–9, various nitrites are shown to react with pyran- and furan-derived cyclopropanes, affording pyrroles with functionalized side chains at C(4). Introduction of a alkyl group at C(5) may resulted in lower yields for entries 8 and 9, but reaction efficiency may be restored when unnecessary ring strain in the starting materials are avoided (see Table 2, entries 10–14). In Table 2, entries 15 and 16, C(5) methylpyrroles were obtained in 55–62% isolated yield without substitution at C(4).

Placing the alkoxy leaving group at the bridgehead of the [3.1.0] bicyclic system permitted the synthesis of 4,5,6,7-tetrahydroindoles (Table 2, entries 17 and 18). Importantly, these synthesized compounds are examples of extremely useful synthetic intermediates in natural product and pharmaceutical chemistry, and can be readily oxidized to the indole. The results in Table 2 reveal the diverse substitution permutations that are possible with the present methodology. Another advantage of the present invention is that the stereochemistry of the cyclopropane appears to have no effect on reaction efficiency. For example, in Table 2, entries 3, 10 and 13, identical yields were obtained whether mixtures or single stereoisomers of cyclopropanes were used.

TABLE 2

Nitrile Cycloadditions with DA Cyclopropanes.

| z | Substrate | Nitrile, RCN | Pyrrole | Isolated Yield |
|---|---|---|---|---|
| 1 | pyran-fused cyclopropane (CO₂Et) | MeCN | 2-R-3-(CO₂Et)-4-(CH₂CH₂CH₂OH)pyrrole | 72% |
| 2 | | PrCN | | 78% |
| 3 | | PhCN | | 58% |
| 4 | | Cl(H₂)₃CN | | 61% |
| 5 | furan-fused cyclopropane (CO₂Et) | MeCN | 2-R-3-(CO₂Et)-4-(CH₂CH₂OH)pyrrole | 52% |
| 6 | | PrCN | | 58% |
| 7 | | MeOCHCHCN | | 81% |

TABLE 2-continued

Nitrile Cycloadditions with DA Cyclopropanes.

| z | Substrate | Nitrile, RCN | Pyrrole | Isolated Yield |
|---|---|---|---|---|
| 8 | | MeCN | | 31% |
| 9 | | PrCN | | 25% |
| 10 | | MeCN | | 93% |
| 11 | | PrCN | | 82% |
| 12 | | PhCN | | 76% |
| 13 | | MeCN | | 98% |
| 14 | | PrCN | | 85% |
| 15 | | MeCN | | 62% |
| 16 | | PrCN | | 55% |
| 17 | | MeCN | | 72% |
| 18 | | PrCN | | 75% |

Table 3 summarizes some of the results from cycloaddition reactions with more densely functionalized cyclopropanes that were prepared from glycals or related structures. These reactions illustrate that the pyrrole synthesis is compatible with a variety of protective groups, including di-tert-butyl silylenes (Table 3, entries 1–4), benzyl ethers (Table 3, entries 4 and 5) and acetates (Table 3, entry 6). The considerable substrate and functional group compatibility is an important asset when preparing more structurally complicated pyrroles.

TABLE 3

Nitrile Cycloadditions with DA Cyclopropanes.

| Entry | Substrate | Nitrile, RCN | Pyrrole | Isolated Yield |
|---|---|---|---|---|
| 1 | | $^t$BuCN | | 87% |
| 2 | | PhCN | | 85% |
| 3 | | p-MeOPhCN | | 93% |

TABLE 3-continued

Nitrile Cycloadditions with DA Cyclopropanes.

| Entry | Substrate | Nitrile, RCN | Pyrrole | Isolated Yield |
|---|---|---|---|---|
| 4 | (structure) | MeCN | (structure) | 87% |
| 5 | (structure) | MeCN | (structure) | 77% |
| 6 | (structure) | MeCN | (structure) | 58% |
| 7 | (structure) | PhCN | (structure) | 82% |

In summary, the tandem donor-acceptor cyclopropane nitrile [3+2] cycloaddition, dehydration and tautomerization strategy of the present invention provides an improved method for pyrrole synthesis that allows precise control over the installation of substituents at three positions around the pyrrole. The method is characterized by operational simplicity, substrate generality, mild reaction conditions and ease of product purification.

The present invention takes advantage of known materials to prepare pyrroles in an efficient and selective manner. For example, many new pyrroles may be prepared with a few hours effort by methods of the present invention.

Methods of the present invention are flexible and offer techniques to prepare many pyrroles that are otherwise difficult to synthesize by standard methods. Additionally, the present invention uses commercially available nitrites at significant cost savings, the synthesis is regiospecific, there is no scrambling of substituents when making compounds of the present invention, yields are generally higher than existing methods, the reaction and reaction conditions do not require any specialized equipment or unusual conditions, all starting materials are easily handled and stable for a long period of time, and further purification steps are made easy (e.g., easier than using condensation reactions because there are fewer by-products). In fact, product purification after pyrrole preparation with the present invention requires about 75% less time as compared with other methods for pyrrole synthesis.

Unlike currently available condensation reactions that are complicated by the formation of numerous by-products, with the present invention, difficult separations are not required, the process is very clean and few by-products result from the synthesis reaction. For example, using traditional methods only a 20% yield of a bispyrrole is generally obtained after two full days of purification involving multiple chromatography runs. With the present invention, the pyrrole product is made with an 85% yield and purified by simple filtration and the whole process takes less than one hour from start-to-finish using bench-stable starting materials.

The cost savings associated with the present invention are apparent when comparing the materials to those used by current methods, such as the Daan van Leusen method—a preparation in which C(3) is an electron withdrawing group, but both C(2) and C(5) cannot be substituted, because one comes from the isocyanide and high yields are only possible when C(4) is aryl. With the van Leusen method, TosMIC is required for activation, a reagent that is at least two to three times more expensive than all the reagents required for use with the present invention. Furthermore, few isocyanides (required for making TosMIC derivatives) are commercially available to extend the van Leusen synthesis, and all are expensive, highly toxic, and emit highly unpleasant odors.

Additional objects, advantages and novel features of the invention as set forth in the description, will be apparent to one skilled in the art after reading the foregoing detailed description or may be learned by practice of the invention. The objects and advantages of the invention may be realized and attained by means of the instruments and combinations particularly pointed out here.

What is claimed is:

1. A method of preparing a di-, tri- and tetrasubstituted pyrrole comprising the step of:
   reacting an alkoxy cyclopropane with a functionalized nitrile in the presence of an effective Lewis acid catalyst.

2. The method of claim 1, wherein the Lewis acid is trimethylsilyl trifluoromethanesulfonate.

3. The method of claim 1, wherein at least one substituent group selected from the group consisting of aryl group, alkyl group, and hydrogen, is selectively positioned in the cyclopropane.

4. The method of claim 3, wherein the position of the substituent in the resulting pyrrole is optionally at the 4-position, the 5-position or both the 4 and 5 positions.

5. The method of claim 1, wherein the stereochemistry of the cyclopropane has no effect on reaction efficiency.

6. The method of claim 1, wherein the pyrrole preparation is compatible with at least one protective group.

7. The method of claim 6, wherein the protective group is optionally a silylene, a benzyl ether or an acetate.

8. The method of claim 1, wherein the pyrrole is unsymmetrical.

9. The method of claim 1, wherein the cyclopropane has a C(2) substituent that is an electron withdrawing group.

* * * * *